United States Patent
Brandon et al.

(10) Patent No.: US 10,383,548 B2
(45) Date of Patent: Aug. 20, 2019

(54) POSTURAL AWARENESS APPARATUS

(75) Inventors: Lee Brandon, Los Angeles, CA (US); Thomas Jackson, La Jolla, CA (US)

(73) Assignee: Lee Brandon, Los Angeles, CA (US)

( * ) Notice: Subject to any disclaimer, the term of this patent is extended or adjusted under 35 U.S.C. 154(b) by 1690 days.

(21) Appl. No.: 12/345,338

(22) Filed: Dec. 29, 2008

(65) Prior Publication Data

US 2009/0177121 A1 Jul. 9, 2009

Related U.S. Application Data

(63) Continuation of application No. PCT/US2006/025587, filed on Jun. 29, 2006, which is a continuation-in-part of application No. 10/712,581, filed on Dec. 11, 2003, now Pat. No. 7,258,653, which is a continuation of application No. 09/553,564, filed on Apr. 20, 2000, now Pat. No. 6,648,838, which is a continuation-in-part of application No. 09/416,160, filed on Oct. 11, 1999, now abandoned, which is a continuation of (Continued)

(51) Int. Cl.
| | |
|---|---|
| A61B 5/103 | (2006.01) |
| A63B 23/02 | (2006.01) |
| A63B 21/00 | (2006.01) |
| A63B 71/06 | (2006.01) |
| A61B 5/00 | (2006.01) |

(52) U.S. Cl.
CPC ........ *A61B 5/103* (2013.01); *A63B 21/00196* (2013.01); *A63B 21/4037* (2015.10); *A63B 23/0244* (2013.01); *A61B 5/6892* (2013.01); *A61B 2562/0252* (2013.01); *A63B 2071/0655* (2013.01); *A63B 2208/0252* (2013.01); *A63B 2220/51* (2013.01); *A63B 2220/56* (2013.01)

(58) Field of Classification Search
CPC ........ A63B 21/00047; A63B 21/00109; A61B 5/4561; A61B 5/103
USPC ...... 600/587, 594; 128/905, 898; 340/573.1, 340/573.7
See application file for complete search history.

(56) References Cited

U.S. PATENT DOCUMENTS

| | | | |
|---|---|---|---|
| 1,904,039 | A | 4/1933 | Brudu |
| 2,742,036 | A | 4/1956 | Montesano |

(Continued)

FOREIGN PATENT DOCUMENTS

| | | |
|---|---|---|
| JP | H05-023402 | 2/1993 |
| JP | H08-299521 | 11/1996 |

OTHER PUBLICATIONS

International Search Report of International Application No. PCT/US06/25587 filed Jun. 29, 2006.

(Continued)

*Primary Examiner* — Daniel L Cerioni
*Assistant Examiner* — Yasmeen S Warsi

(57) ABSTRACT

A postural awareness apparatus includes a pad, a signal producing system, and an activator that activates the signal producing system when a compressive force applied to the apparatus exceed a predetermined compressive force. The activator includes a switch having an upper portion, a compressible element having defined therein an opening, the compressible element at least partially surrounding the upper portion of the switch, and a cap adapted to secure the compressible element in a position at least partially surrounding the upper portion of the switch.

15 Claims, 15 Drawing Sheets

Related U.S. Application Data application No. 09/023,038, filed on Feb. 13, 1998, now Pat. No. 6,019,738.

(56) References Cited

U.S. PATENT DOCUMENTS

| | | | |
|---|---|---|---|
| 2,780,693 A | 2/1957 | McClellan | |
| 3,042,025 A | 7/1962 | Jackson | |
| 3,325,799 A | 6/1967 | Farris | |
| 3,582,935 A | 6/1971 | Verhaeghe | |
| 3,608,541 A | 9/1971 | Hall | |
| 3,981,032 A | 9/1976 | Brooks | |
| 4,108,164 A | 8/1978 | Hall, Sr. | |
| 4,326,506 A | 4/1982 | Kawabata | |
| 4,581,677 A * | 4/1986 | Hruby | G01D 5/2417 177/210 C |
| 4,592,345 A | 6/1986 | Wahl | |
| 4,617,525 A | 10/1986 | Lloyd | |
| 4,730,625 A * | 3/1988 | Fraser et al. | 600/594 |
| 4,762,134 A * | 8/1988 | Gala | A61B 5/1104 600/594 |
| 4,827,763 A * | 5/1989 | Bourland | A61B 5/6892 361/283.1 |
| 4,858,620 A | 8/1989 | Sugarman | |
| 4,895,160 A | 1/1990 | Reents | |
| 4,996,865 A * | 3/1991 | Haulsee et al. | 72/349 |
| 5,062,169 A * | 11/1991 | Kennedy | A47C 27/082 5/713 |
| 5,113,176 A * | 5/1992 | Harris | 340/573.7 |
| 5,146,929 A | 9/1992 | Sawhill | |
| 5,161,543 A | 11/1992 | Abramson | |
| 5,163,195 A | 11/1992 | Hill | |
| 5,267,857 A | 12/1993 | Sickler | |
| 5,279,310 A | 1/1994 | Hsien | |
| 5,343,876 A | 9/1994 | Rogers | |
| 5,469,861 A | 11/1995 | Piscopo et al. | |
| 5,515,865 A | 5/1996 | Scanlon | |
| 5,522,401 A | 6/1996 | Brucker | |
| 5,545,125 A | 8/1996 | Tseng | |
| 5,570,301 A | 10/1996 | Barrus | |
| 5,643,329 A | 7/1997 | Solomonow et al. | |
| 5,684,460 A | 11/1997 | Scanion | |
| 5,713,841 A | 2/1998 | Graham | |
| 5,805,142 A * | 9/1998 | Byrne | 345/163 |
| 5,858,552 A | 1/1999 | Bader et al. | |
| 5,890,694 A | 4/1999 | Possick | |
| 5,970,789 A * | 10/1999 | Meyer | A47C 31/123 73/172 |
| 5,993,400 A * | 11/1999 | Rincoe | A61B 5/1036 73/172 |
| 6,019,738 A | 2/2000 | Brandon | |
| 6,159,172 A * | 12/2000 | Gray et al. | 601/149 |
| 6,204,767 B1 | 3/2001 | Sparks | |
| 6,348,663 B1 | 2/2002 | Schoos et al. | |
| 6,356,194 B1 | 3/2002 | Fukui et al. | |
| 6,533,742 B1 * | 3/2003 | Gach, Jr. | 602/23 |
| 6,585,391 B1 * | 7/2003 | Koch | F21L 4/005 200/512 |
| 6,648,838 B1 | 11/2003 | Brandon et al. | |
| 6,682,351 B1 | 1/2004 | Abraham | |
| 6,894,271 B2 | 5/2005 | Widzgowski | |
| 2003/0077931 A1 | 4/2003 | Hida | |
| 2004/0097837 A1 | 5/2004 | Brandon et al. | |

OTHER PUBLICATIONS

Office action for related PRC Application No. 200680055666.0, issued Apr. 20, 2011.

English translation of Office action received in related PRC Application No. 200680055666, issued Mar. 28, 2012, received by US counsel Apr. 4, 2012.

Office action received in related Australian Application No. 2006345722, issued Mar. 16, 2012, received by US counsel Apr. 10, 2012.

Office action received in related PRC Application No. 200680055666, dated Oct. 31, 2012.

Japanese Patent Office, Official Notice of Rejection dated Apr. 17, 2012 in corresponding Japanese patent application No. 2009-518076.

* cited by examiner

POSTURAL AWARENESS APPARATUS

CROSS REFERENCE TO RELATED APPLICATIONS

This application is continuation of PCT/US2006/025587, which is a continuation-in-part of 10/712,581, filed Dec. 11, 2003, now U.S. Pat. No. 7,258,653; which is a continuation of Ser. No. 09/553,564, filed Apr. 20, 2000, now U.S. Pat. No. 6,648,838; which is a continuation-in-part of 09/416,160, filed Oct. 11, 1999, now abandoned; which is a continuation of Ser. No. 09/023,038, filed Feb. 13, 1998, now U.S. Pat. No. 6,019,738, the contents of each of which are incorporated by reference in their entirety.

FIELD OF THE INVENTION

The present invention relates to devices for strengthening the spine, abdomen and posture on multiple planes, and for teaching a neutral spine.

BACKGROUND OF THE INVENTION

Devices for monitoring, controlling and correcting posture are described, for example, in U.S. Pat. No. 3,582,935, to Verhaeghe; U.S. Pat. No. 3,981,032, to Brooks; U.S. Pat. No. 4,730,625, to Fraser et al.; U.S. Pat. No. 5,146,929, to Sawhill; U.S. Pat. No. 5,279,310, to Hsien; and U.S. Pat. No. 5,522,401, to Brucker. However, such corrective devices are not designed specifically for use in strengthening the abdomen and spine of the user.

U.S. Pat. No. 6,019,738, to Brandon, issued Feb. 1, 2000, which is incorporated herein in its entirety by reference, disclosed the first successful postural awareness apparatus useful in an exercise regimen for strengthening the abdomen and spine of a human. The disclosed apparatus includes a pad having a longitudinal axis, signal means for producing a signal, and detection means for detecting a weight (i.e., a compressive force) applied to the pad and activating the signal means when the weight exceeds a predetermined weight. The signal means include a plurality of vibrator units, a portion of the plurality of vibrator units being affixed to the pad at opposed locations on either side of the longitudinal axis. Further refinements of the postural awareness apparatus were disclosed in U.S. Pat. No. 6,648,838, to Brandon et al., issued Nov. 18, 2003, and in co-pending U.S. patent application Ser. No. 10/712,581, filed Nov. 12, 2003, the entire disclosures of both of which are incorporated herein in their entireties by reference.

A continuing need exists for improved devices that are useful in an exercise regimen for strengthening the abdomen and spine of a human. A need also exists for an apparatus that informs the user when the neutral spine position is maintained during exercise in multiple positions (e.g., sitting, lying, standing).

SUMMARY OF THE PREFERRED EMBODIMENTS

In accordance with one aspect of the present invention, there is provided an apparatus that includes a pad, a signal producing system, and an activator which responds to a compressive force and which activates the signal producing system when a compressive force applied to the apparatus exceeds a predetermined compressive force. The activator includes a switch having an upper portion, a compressible element having defined therein an opening, the compressible element at least partially surrounding the upper portion of the switch, and a cap adapted to secure the compressible element in a position at least partially surrounding the upper portion of the switch.

According to more specific embodiments, the postural awareness apparatus further includes a low back assembly. The low back assembly can be releasably affixed to the pad, in particular embodiments, or permanently affixed to the pad in other particular embodiments. In further particular embodiments, the low back assembly includes a base having defined therein at least one opening within which the switch is disposed, and a cushion having defined therein at least one opening aligned with the opening in the base. The base includes a raised portion in which the opening is defined, and the switch is disposed within the opening and extends through the base. The cap has an upper element and a plurality of arms, each of the arms having a distal end including a locking element. The switch and the compressible element have substantially collinear longitudinal axes.

According to such specific embodiments, the compressible element is disposed between the base and the upper element of the cap. Each of the arms of the cap extends through an opening defined in the base, and the locking elements of the cap prevent unintentional disengagement of the cap from the base while permitting motion of the cap relative to the base substantially in the direction of the longitudinal axes of the switch and the compressible element. This permits the upper element of the cap to contact, and thus activate, the switch when a compressive force in excess of the predetermined value is applied to the upper element of the cap. This further permits the compressible element to be removed and replaced with another compressible element, for example, a compressible element having a different stiffness.

Further more specific embodiments of the inventive apparatus include a plurality of activators. In these embodiments, the pad has a longitudinal axis and a portion of the plurality of activators are located at opposed locations on either side of the longitudinal axis.

According to additional specific embodiments, the signal producing system comprises a plurality of vibrator units. More particularly, a portion of the plurality of vibrator units are affixed to the pad (for example, by virtue of being incorporated into the low back assembly) at opposed locations on either side of the longitudinal axis.

Certain of the foregoing embodiments of the inventive apparatus include a pad to which a low back assembly is affixed. The low back assembly can also be employed independently of the pad. Thus, in accordance with another aspect of the present invention, there is provided a postural awareness apparatus adapted to contact a portion of the lower back of a human user. The apparatus includes a base having defined therein at least one opening, a cushion having defined therein at least one opening aligned with the opening in the base, a signal producing system, and an activator that activates the signal producing system when a compressive force applied to the apparatus exceeds a predetermined compressive force. The activator includes a switch having an upper portion, the switch being disposed within the opening defined in the base; a compressible element having defined therein an opening, the compressible element at least partially surrounding the upper portion of the switch; and a cap adapted to secure the compressible element in a position at least partially surrounding the upper portion of the switch. The cap, in particular embodiments, is removable to permit interchange of the compressible element.

Other features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

The present invention provides devices and methods for strengthening the spine and abdomen, and for teaching the user postural awareness in order to maintain and strengthen a neutral spine. By "neutral spine" is meant a biomechanically correct spinal position in which muscular balance is maintained and the spine absorbs forces optimally and is neither in extreme flexion nor extreme extension. For example, typical flexion/extension biases for a healthy user is about 30° and about 15°, respectively; other users may have greater or lesser flexion/extension biases. Neutral spine positions vary with the posture of the user; for example, the neutral spine position of a user with kyphosis will differ from the neutral spine position of a user having a normal posture.

Figure 1A:
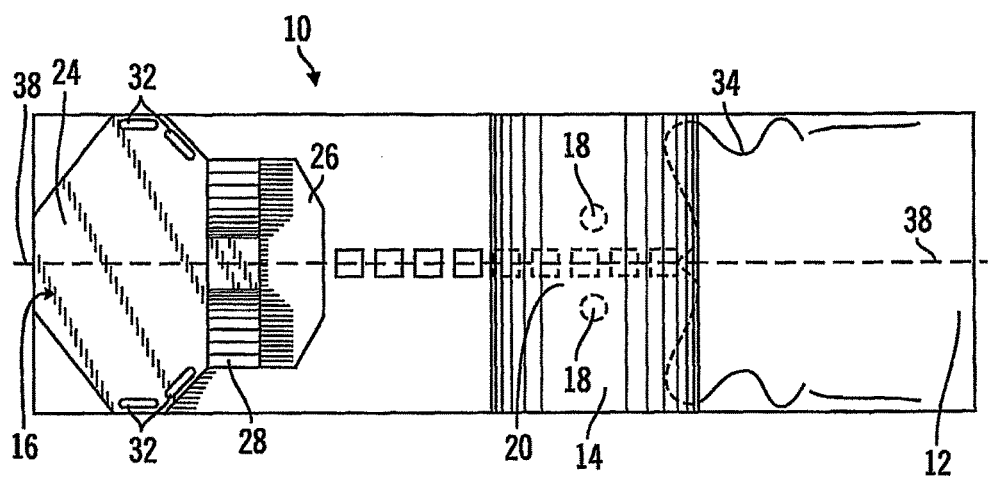
FIGS. 1a-b are top plan and exploded side views, respectively, of a first embodiment employing a detachable head rest and a lumbar pad, with vibrator units and pressure sensors disposed within the lumbar unit shown in phantom.
Figure 1B:
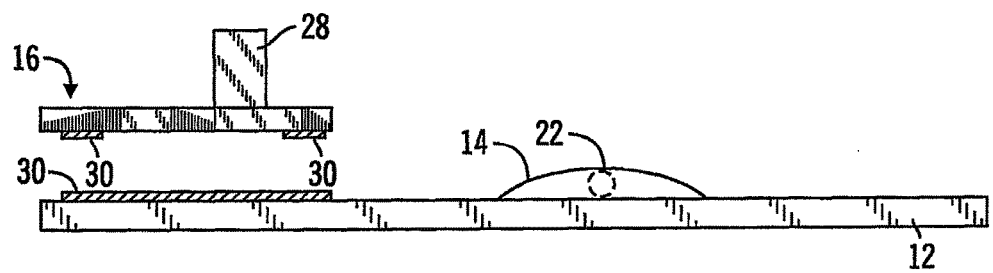
Figure 2A:
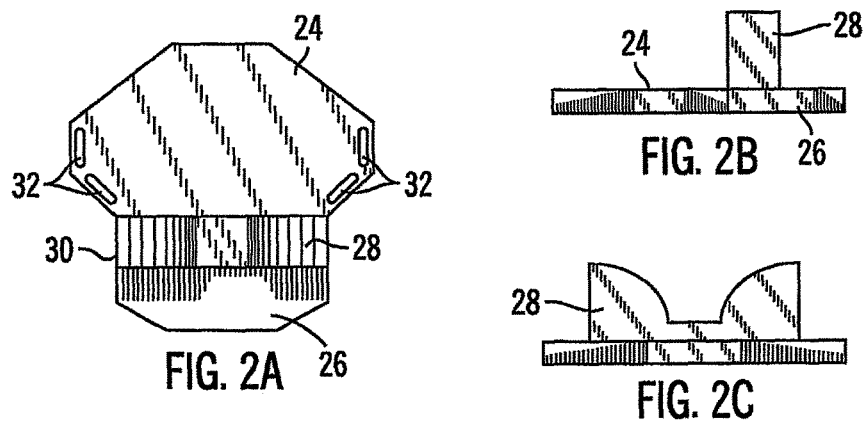
FIGS. 2a-c are top, side and end views of a detachable head rest employed with the embodiments of FIGS. 1a-b.
Figure 2B:
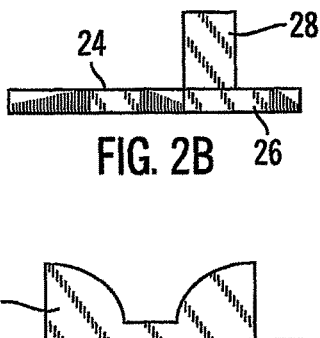
Figure 2C:
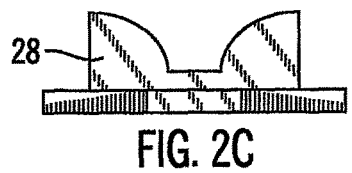
Figure 3:
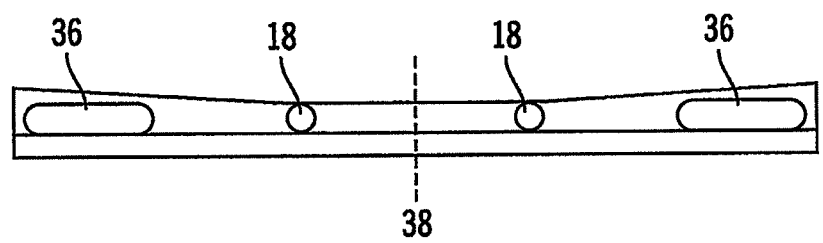
FIG. 3 is a sectional view of the lumbar pad of FIGS. 1a-b showing the location of pressure sensors and vibrator units within the pad.

Turning now to the figures, in FIGS. 1-3, a first embodiment of an apparatus 10 of the invention includes a mat 12, preferably comprised of a non-slip material, with a lumbar pad 14 and a head support 16.

Lumbar pad 14 preferably is unitary with mat 12, that is, is formed from a section of mat 12. Disposed within lumbar pad 14 are activator 18, which detects a weight applied to a surface 20 of lumbar pad 14 and subsequently activates signal producing system 22. The activator 18 can include elements such as one or more mechanical switches, one or more pressure sensors, or other devices known to those skilled in the art for detecting a weight applied to a surface.

The activator 18 is connected to one or more signal producing systems 22. The signal producing system(s) 22 are activated when a compressive force (e.g., a weight) is applied to the selected activator 18, that is, when the activator responds to (i.e., detect) a weight applied to the surface 20 of mat 12. Once activated, the signal producing system 22 produce a signal that is perceptible by a person using the inventive apparatus.

In certain more particular embodiments, activator 18 responds to a compressive force (e.g., weight) that is within a desired range. Thus, when the applied compressive force is below the minimum of the desired range, the activator 18 is not activated, and when the applied compressive force is above the maximum of the desired range, the activator 18 is deactivated. In such embodiments, the range of compressive forces to which activator 18 responds can be determined in any conventional manner (e.g., via electronic elements, software, mechanical switches or other devices, etc.)

Exemplary signal producing systems 22 include, without limitation, devices for producing a vibratory signal, such as a mechanical vibrator; devices for producing an auditory signal, such as an electronic tone generator; devices for producing a visible signal, such as a light bulb or a light-emitting diode (LED); and the like, as well as combinations of such devices. The signal producing system 22 can be affixed to or within the apparatus 10, for example within lumbar pad 14, or can be located externally. The activator 18 and the signal producing system 22 are connected together, for example as parts of an electrical circuit, or by means such as low-power radio transmitters. Any devices, elements or apparatus for enabling activator 18 to activate signal producing system 22 are considered to be within the scope of the present invention.

Optionally, lumbar pad 14 can accommodate one or more lordosis inserts 14*a* disposed above activator 18 in order to support users having excessive lordotic sway or other excessive flexion or extension bias. Exemplary inserts include, without limitation, mechanical inserts, pneumatic or other inflatable inserts, and the like. Lumbar pad 14 can also optionally include a switch (not shown) for disabling signal producing system 22 to allow use of the apparatus without generation of a signal.

Head support 16 includes a head/neck base 24 and a cervico-thoracic support 26. A neck support 28, which optionally is adjustable in width, is disposed on head support 16 between head/neck base 24 and cervico-thoracic support 26. As illustrated in FIG. 1*b*, head support 16 is detachably affixed to mat 12 by attachment device 30, for example hook/loop devices such as Velcro® fasteners, snaps, etc., in order to allow selectable positioning of the head support 16, and also to allow head support 16 to be used separately if desired. In the alternative, head support 16 can be permanently affixed to mat 12.

In a preferred embodiment, head support 16 is provided with a plurality of handles 32. Handles 32 can be formed by cutting openings in base 24, for example, or can be separately formed and affixed to base 24.

If desired, mat surface 20 can be provided with graphics 34, such as a stylized representation of a human pelvis and lower backbone, in order to facilitate orientation of a user with respect to the mat surface. Illustrations of the positions of TLC pressure points and the locations of the activator 18 are also beneficial to assist the user in properly orientation with respect to the apparatus 10.

In a preferred embodiment illustrated in FIG. 3, signal producing system 22 include two vibrators 36 disposed within lumbar pad 14 along either side of the longitudinal axis 38 of mat 12. Vibrators 36 are connected to activator 18 and are activated when activator 18 responds to a compressive force (e.g., the weight of a user's body) applied to the surface 20 of mat 12.

Figure 6A:
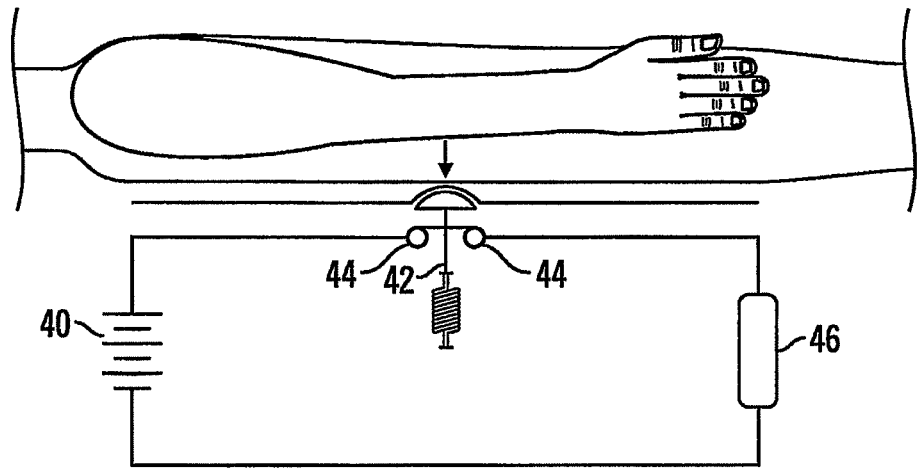
FIGS. 6a-b are schematic diagrams showing a mechanical switch useful as a pressure sensor, showing activated and inactivated states.
Figure 6B:
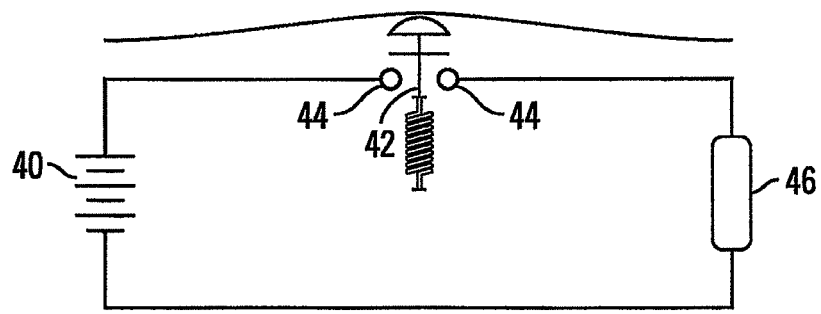

An example of an activator 18, illustrated in FIGS. 6*a-b*, includes a power source 40, which can be a battery disposed, for example, within lumbar support 14 or at another location within, on or external to apparatus 10, or A/C power supplied via a plug; a mechanical switch 42 energized by a spring having a preselected spring constant; and a pair of contacts 44, which with signal producing system 22, such as a vibrator, form a circuit. In FIG. 6*a*, a weight, for example the weight of a user's body (indicated by a downward arrow), exceeds the spring force and causes the mechanical switch 42 to close, closing the circuit and activating signal producing system 22. Thus, when the user remains in contact with activator 18, the circuit remains closed and the signal producing system 22 remains activated. When the signal producing system includes a vibrator unit 46 (shown in FIGS. 6*a-b*), the user perceives a vibratory signal applied to his back; in the alternative, when the signal producing system 22 includes a tone generator, light bulb, or LED, the user hears and/or sees the signal generated by the signal producing system 22. In any event, the user is informed when his back is in contact with the activator 18 and exerts sufficient downward force to cause switch 42 to close.

An alternative embodiment of activator 18 includes a pressure sensor and an associated electronic circuit in place of the mechanical switch. Such accompanying circuits are readily produced by those skilled in the art to generate an output signal in response to application of a predetermined pressure to the pressure sensor. This output signal in turn activates signal producing system 22.

Figure 7:
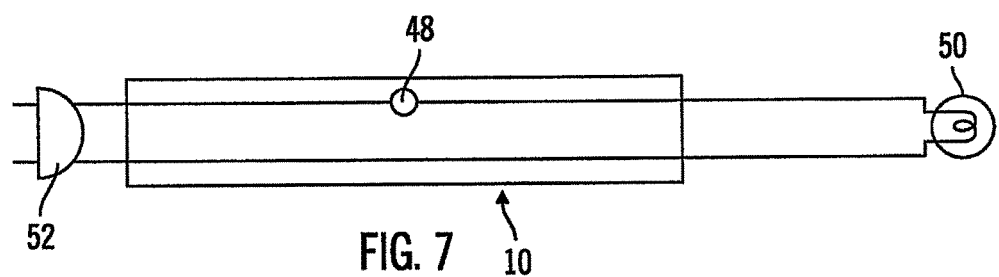
FIG. 7 is a schematic diagram of a pressure sensor with a light-generating signal producing system and an external power supply.

FIG. 7 illustrates another embodiment of the inventive apparatus in which a pressure sensor 48 is employed rather than a mechanical switch. The signal producing system includes a light bulb 50. Power is supplied from an external A/C power supply via plug 52.

Optionally, a kyphosis wedge 54 is inserted between head support 16 and mat 12, to accommodate users with a head-forward position.

Figure 4A:
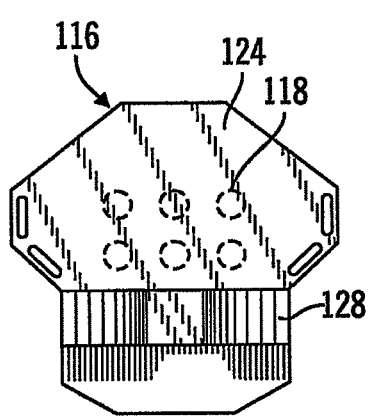
FIGS. 4a-c are top, sectional and side views of an alternative embodiment of a head rest with separate pressure sensors, vibrator units and a control switch.
Figure 4B:
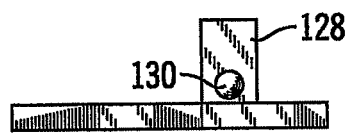
Figure 4C:
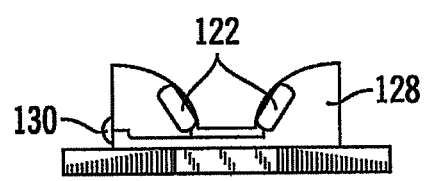
Figure 5:
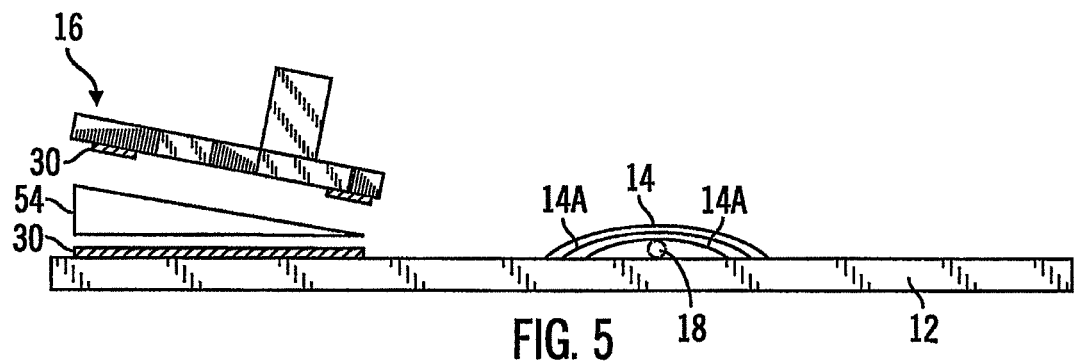
FIG. 5 is a side exploded view of an alternative embodiment including a kyphosis wedge.

FIGS. 4*a-c* illustrate an alternative embodiment of a head support 116 which includes activator 118 disposed within head/neck base 124, and one or more signal producing systems 122. As illustrated, the signal producing systems includes a plurality of vibrators disposed within neck support 128. Activator 118 activates the signal producing systems 122 (e.g., vibrators) when the user's head leaves contact with activator 118. For example, when activator 118 includes a mechanical switch, the switch is in an open position when the user's head is in contact with it, rather than in a closed position as with activator 18 described above. When activator 118 includes a pressure sensor, the accompanying electronic circuit produces a signal when the pressure detected falls below a predetermined level, rather than exceeding a predetermined level.

If desired, a 3-way switch 130 can be connected to activator 118 and the vibrators. The switch 130 allows the user to selectively enable or disable the activator 118 and to separately control activation of the vibrators. Thus, in one position, the activator 118 are enabled to activate the vibrators as described above with respect to activator 18 and signal producing system 22. In a second position, the activator 118 are disabled, and the vibrators are deactivated. In a third position, the activator is disabled, and the vibrators are activated, thus allowing selective user relaxation and the option to stretch while using the inventive apparatus in between exercise drills.

Figure 8:
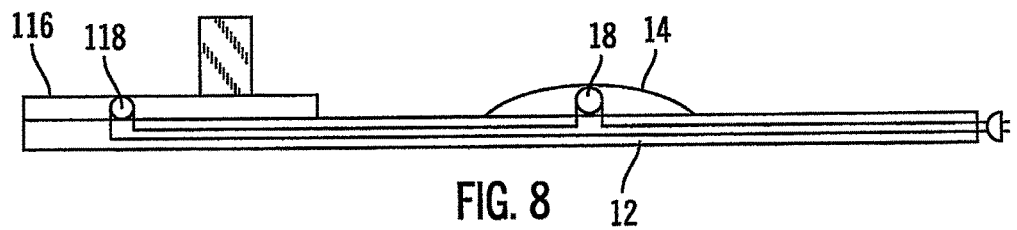
FIG. 8 is a schematic diagram of an alternative embodiment in which two pressure sensors are employed in sequence, one in the head rest and one in the lumbar pad.
Figure 9:
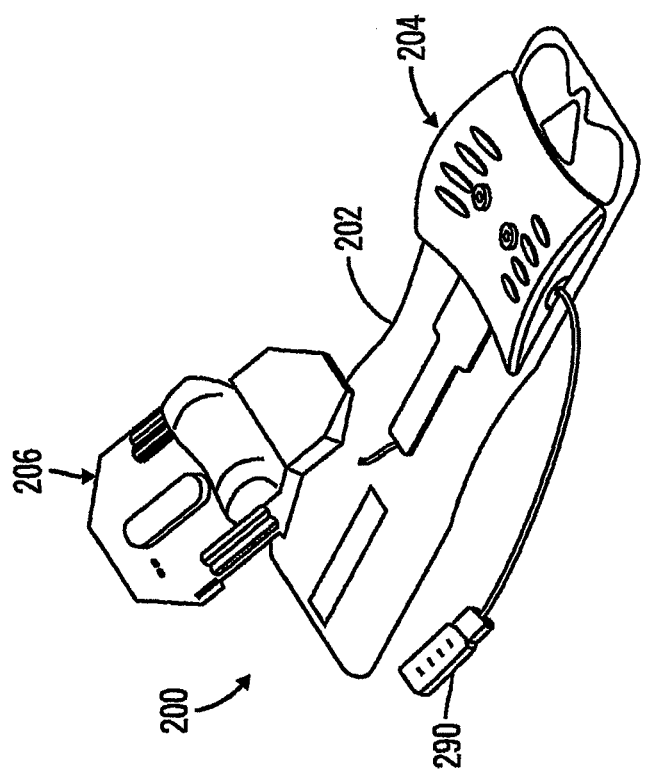
FIG. 9 is a partially exploded left perspective view of another embodiment of the inventive apparatus including separable head/neck and low back assemblies.
Figure 10A:
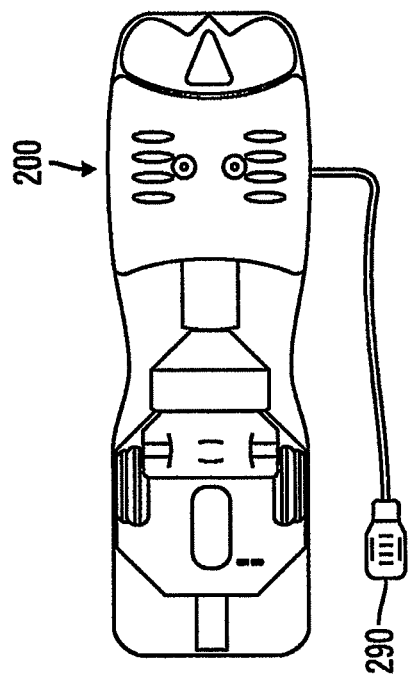
FIG. 10(a)-(b) are top plan views showing the positioning of the head/neck assembly relative to the low back assembly for short and tall users, respectively.
Figure 10B:
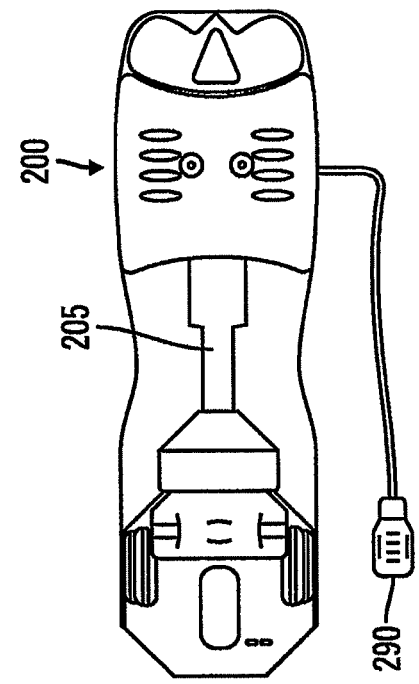

The activator 118 in the foregoing embodiment of the head support 116 can be connected in series to the activator 18 disposed, for example, within lumbar support 14 as shown in FIG. 8. In this embodiment, the signal producing system 22 (and optionally vibrators disposed within head support 116) are activated only when both activator 118 and activator 18 are affected by a compressive force, such as the weight of a user's head and body, respectively.

The signal (vibratory, auditory, visual, etc.) provided by the inventive apparatus allows the user to heighten the intensity of muscles being worked by eliminating momentum. When in use, the signal informs the user that his thoraco-lumbar area compresses the activator 18 sufficiently to ensure the isolation of the correct muscle usage. Thus, the user's proprioceptive acuity is heightened for lumbo-sacral coordination and strengthening.

The inventive apparatus preferably is used on a horizontal surface such as a floor or exercise bench. If desired, mat 12 can be provided with one or more attachment devices such as a hook or clamp, which allows the apparatus to be affixed to a vertical surface such as a door. The apparatus can also be used on surfaces such as chairs.

The signal provided by the inventive apparatus constitutes feedback to the user while exercising, which permits the user to minimize momentum and maximize intensity. To begin exercise using the inventive apparatus in a supine position, the user's third lumbar vertebra (L3) (typically in the vicinity of the user's belt line or umbilicus) is lined up with the lumbar pad 14, and the head/neck support 16 is positioned under the user's neck where it is comfortable. If necessary, the position of the head/neck support 16 is adjusted to accommodate the user. In use, the low back is compressed into lumbar pad 14 until a signal is generated by the signal producing system 22. Constant tension is maintained isometrically by tightening the involved muscles.

Use of the alternative embodiment of the head/neck support 116 permits the user to avoid neck strain. If the user lifts his head during abdominal training, resulting in neck strain, the head lift is signaled to the user by the signal producing system 122, such as a vibration to the neck, an audible signal produced by a buzzer, or any other desired signal producing system. The user can then lower his head to contact the head/neck support 116.

A further particular embodiment 200 of an apparatus according to the invention is illustrated in FIGS. 9-16. Apparatus 200 includes a mat 202, a low back assembly 204 and a head/neck assembly 206. Both the low back assembly 204 and the head/neck assembly 206 can be releasably secured to mat 202, for example via Velcro® strips or other fasteners. In specific embodiments, low back assembly 204 is secured, either permanently or releasably, to a predetermined location on mat 202, and head/neck assembly 206 is releasably secured to mat 202 at a selectable distance from low back assembly 204. Thus, as illustrated in FIGS. 10a-b, the apparatus can calibrated to accommodate users of varying stature, with the head/neck assembly 206 being moved closer to mid-pad 205 and thus secured to mat 202 closer to low back assembly 204 to accommodate short users (see FIG. 10a), or farther from mid-pad 205 and low back assembly 204 to accommodate tall users (see FIG. 10b).

Figure 11:
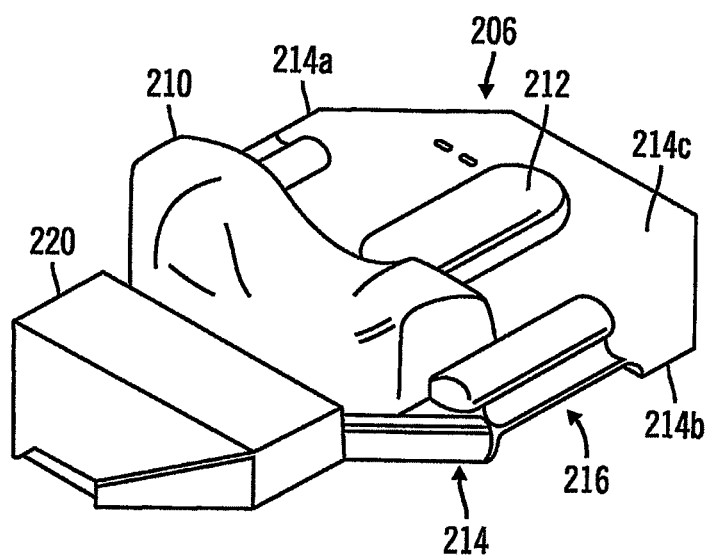
FIG. 11-13 are, respectively, a right perspective, bottom plan and exploded view of the head/neck assembly of FIG. 9.
Figure 12:
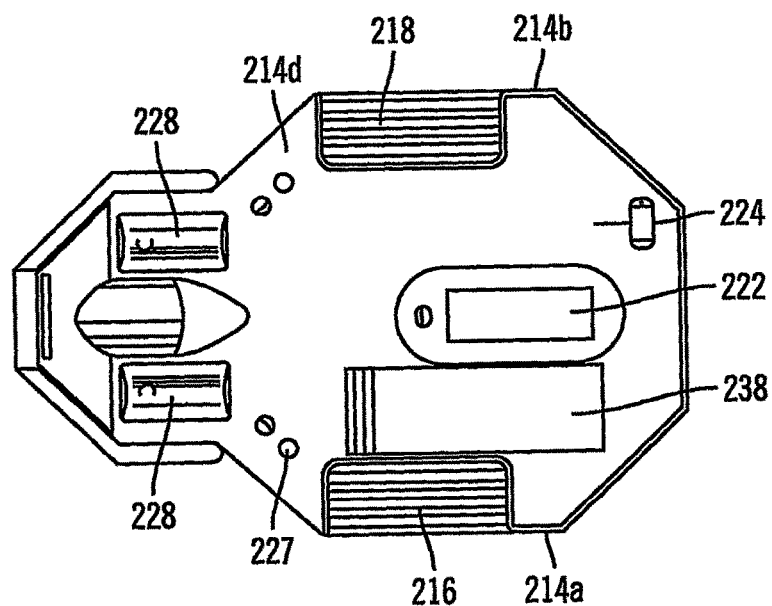
Figure 13:
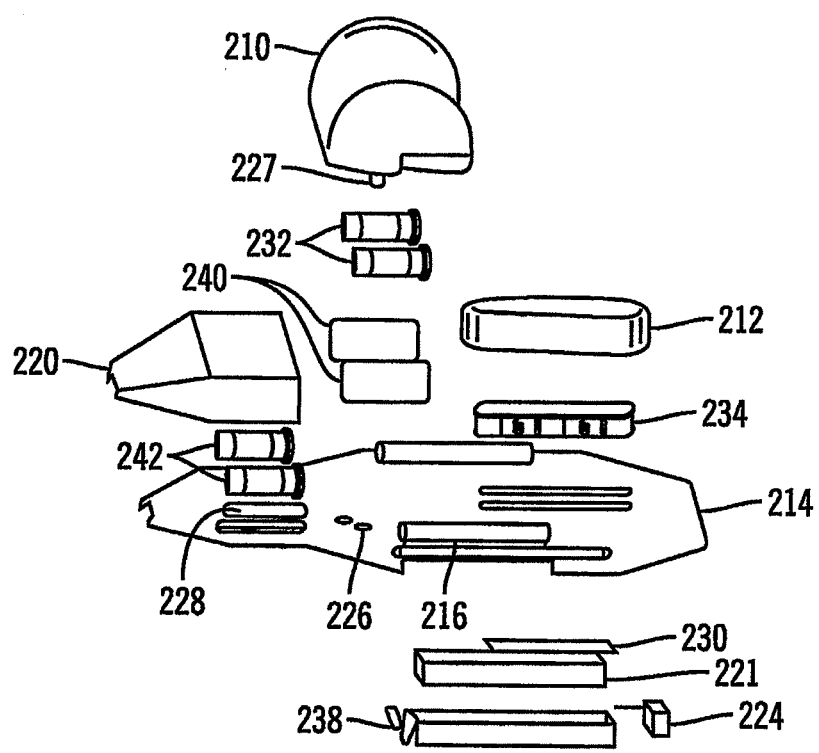

A particular embodiment of head/neck assembly 206 useful with the foregoing embodiment 200 of the inventive apparatus (as well as the previously described embodiment 10) is illustrated in FIGS. 11-13. Head/neck assembly 206 includes neck roll 210 and head sensor pad 212 (covering head switch 234) mounted on neck board 214. Neck roll 210 and head sensor pad 212 are, in particular embodiments, formed from resilient materials such as polyurethane or other foam, or in the alternative include a resilient inner material and an outer layer formed from leather, fabric, vinyl or other suitable covering material. Neck vibrators 232, more particularly paired units as illustrated, are secured beneath neck roll 210 by motor backups 240. Aligning elements 227 of neck roll 210 register within holes 226 defined in neck board 214.

Handles 216 are defined along sides 214a-b of neckboard 214. Downward-opening concavities 218, which in particular embodiments such as here illustrated extend beyond the upper surface 214c of neck board 214, are formed in the lower surface 214d of neck board 214 and receive the user's fingers when the user grips handles 216. Upper back pad 220 is also secured to neck board 214. Upper back vibrators 242 are disposed within cavities 228 and sandwiched between neck board 214 and upper back pad 220.

Securing device 222, for example a Velcro® strip, are affixed to lower surface 214d of neck board 214, and enable head/neck assembly 206 to be releasably affixed to main pad 202.

In further particular embodiments a battery pack 221, secured to the neck board 214 by battery cover 238 and Velcro® strip 230, provides power to the upper back vibrators 242 and neck vibrators 232, and in additional particular embodiments to buzzer 224. Alternatively, a battery pack can be secured to or within low back assembly 204. If desired, multiple battery packs can be used.

Figure 14:
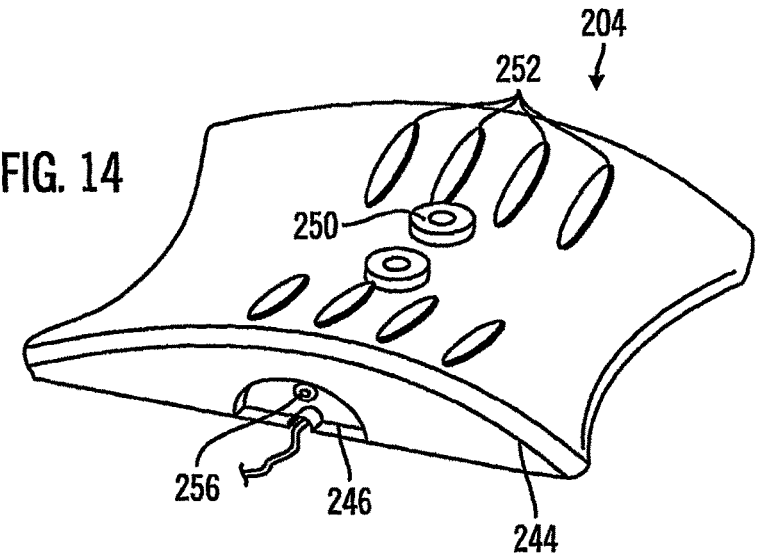
FIG. 14 is a left perspective view of an embodiment of the low back assembly of FIG. 9.
Figure 15:
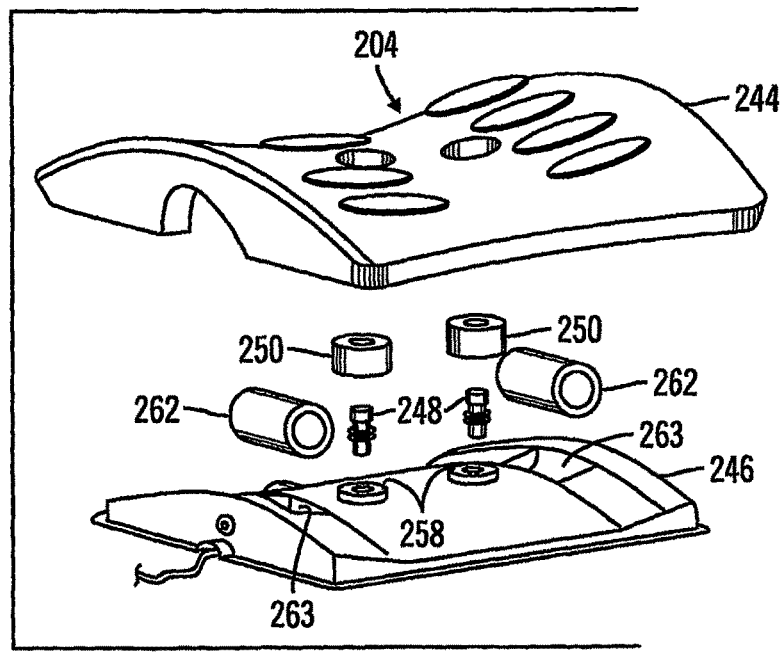
FIG. 15 is an exploded perspective view of the low back assembly of FIG. 14.
Figure 16:
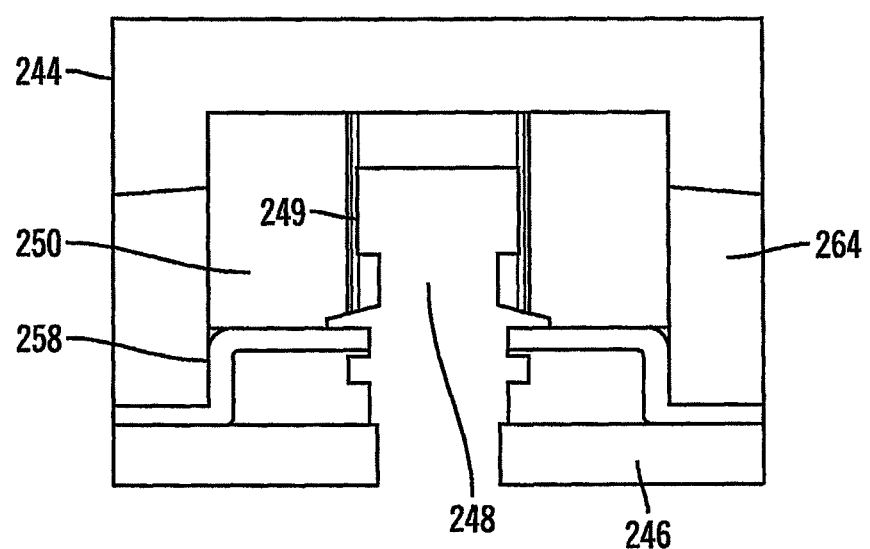
FIG. 16 is a cross-sectional view of a portion of the low back assembly of FIG. 14 through a switch/force adjustment system including a switch and force adjusting ring.

Turning to FIGS. 14-16, low back assembly 204 includes outer cushion 244, which can in particular embodiments be formed from a resilient material such as polyurethane or other foam material, or in the alternative include a resilient inner material and an outer layer formed from leather, fabric, vinyl or other suitable covering material, or a skinned foamed material such as a skinned polyurethane foam produced by an injection molding process. Outer cushion 244 is secured to shell 246 serving as a rigid support, either directly or via an additional intermediate cushioning layer 264 (see FIG. 16). In particular embodiments, the upper surface of outer cushion 244 includes a plurality of positioning ridges 252, which provide increased sensitivity to the user and enable the user to more easily position his or herself properly atop the low back assembly 204.

Lower back vibrators 262, more particularly paired vibrators as illustrated in FIG. 15, are disposed in cavities 263 between outer cushion 244 and shell 246. Vibrators 262 are activated by a switch/force adjustment system (described below). Vibrators 262 can be powered, in particular embodiments, by a battery pack or packs similar to those used in the head/neck assembly 206 described above. Alternatively, vibrators 262 can be powered from a wall socket, an automobile cigarette lighter plug, an external battery or battery pack, or any other desired external source via system power connection 256.

A first embodiment of a switch/force adjustment system according to the present invention is shown in FIGS. 15-16. In this embodiment, switches 248 are disposed in switch mounts 258 which in particular embodiments are integral with shell 246, and which in alternative particular embodiments are separate elements that are secured to shell 246. Surrounding and engaging the upper portion 249 of switch 248 is a force adjustment ring 250, which in turn registers within and protrudes upward from opening 260 defined in outer cushion 244.

Force adjustment ring 250 is comprised, in particular embodiments, of a resilient material that is stiffer and less resilient than the material(s) comprising cushion 244. By varying the stiffness of force adjusting ring 250, the magnitude of the compressive force required to dose switches 248 and thus activate vibrators 262 can be selectively controlled. For example, a user can sequentially employ force adjusting rings 250 of gradually increasing stiffness, in order to gradually increase the compressive force that the user's back must exert on the switch/force adjustment systems in order to activate the vibrators 262.

As illustrated, switches 248 and force adjusting rings 250 are employed in the low back assembly 204. In other particular embodiments, switches 248 and force adjusting rings 250 are also used in the head/neck assembly 206 in order to activate vibrators 232 and/or 242.

Figure 17:
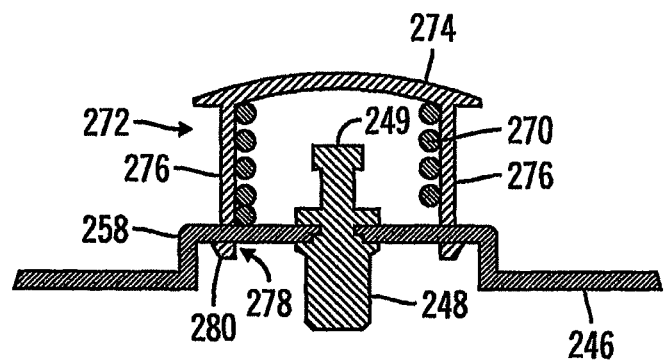
FIG. 17 is a cross-sectional view of an alternative embodiment of a switch/force adjustment system including a switch, a cap and a spring.
Figure 18:
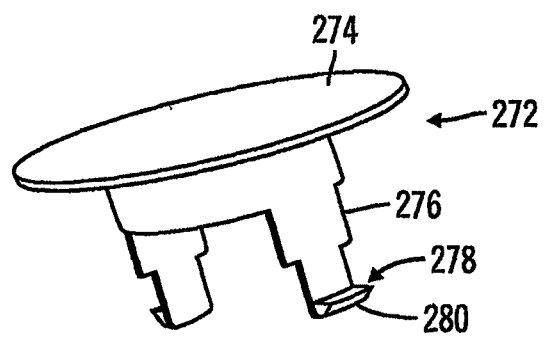
FIG. 18 is a perspective view of the cap of FIG. 17.
Figure 19:
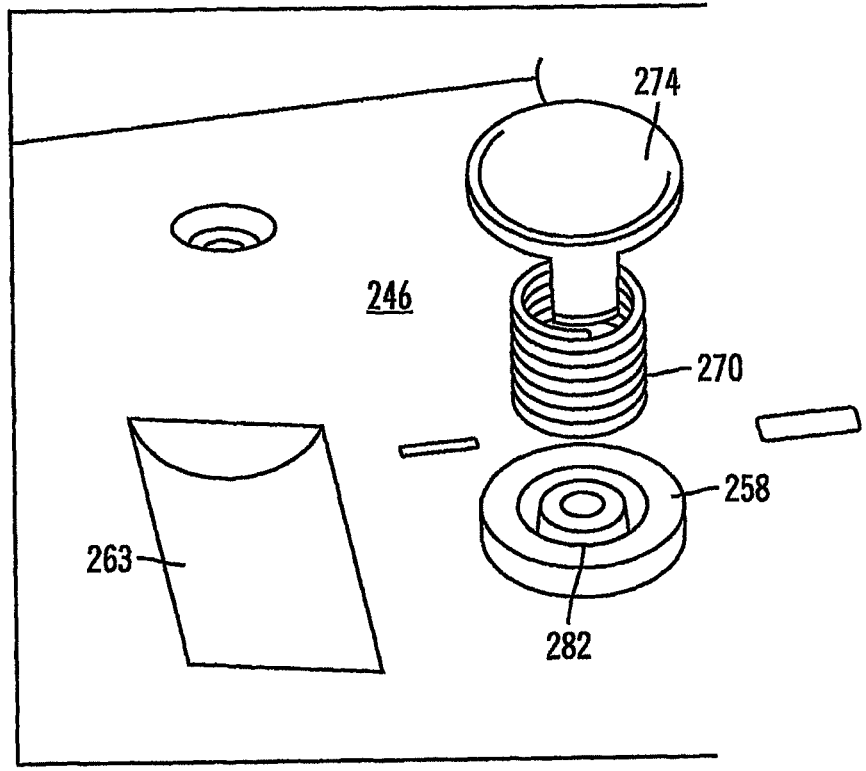
FIG. 19 is a perspective view illustrating the arrangement of the spring and cap of FIG. 17 with respect to the base of the low back assembly.

A second embodiment of a switch/force adjustment system according to the present invention is shown in FIGS. 17-19. In this embodiment, upper portion 249 of switch 248 is surrounded by a compressible element 270, as illustrated a spring. Switch 248 and compressible element 270 each have longitudinal axes, and the respective axes are substantially collinear when compressible element 270 is disposed about switch 248. Cap 272 including upper element 274 and a plurality of arms 276 (two are illustrated in FIGS. 17-18) is disposed above compressible element 270 such that upper element 274 is in contact with the top of compressible element 270 and together with arms 276 at least partially encloses compressible element 270. Distal ends 278 of arms 276 include locking elements 280 which engage switch mounts 258 via notches 282. Sufficient space is provided within switch mounts 258 to permit movement of arms 276 in a direction substantially parallel to the longitudinal axis of switch 248. Cap 272 registers within and protrudes upward from opening 260 defined in outer cushion 244. Locking elements 280 of cap 272 prevent unintentional disengagement of cap 272, while permitting the cap to be removed (i.e., by squeezing arms 276 toward each other) in order to remove and/or replace compressible element 270.

In use, exertion of a compressive force on cap 272 causes a downward displacement of the cap, which brings the cap into contact with switch 248. The stiffness of the compressible element 270 determines the amount of compressive force needed to cause switch 248 to close and thereby activate vibrators 262. A user thus can sequentially employ compressible elements 270, such as springs, of gradually increasing stiffness, in order to gradually increase the compressive force that the user's back must exert on the switch/force adjustment systems in order to activate the vibrators 262.

Vibrators 262 are activated by switches 248. In more particular embodiments using at least one pair of vibrators 262, each of the vibrators is separately and independently operable by the user. In other particular embodiments, the vibrators can be configured to work in tandem rather than independently.

Figure 20:
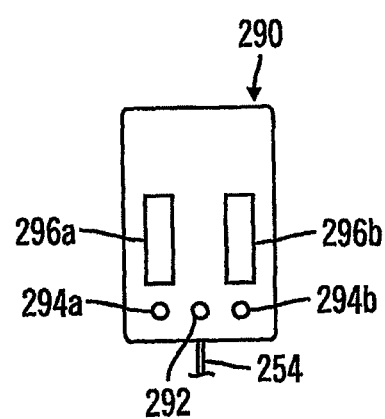
FIG. 20 is a schematic of a control unit useful with embodiments of the inventive apparatus.

In particular embodiments, one or more of the vibrators 262 can also be activated manually by means of a control unit 290 (e.g., a hand set as shown in FIG. 20) in communication with the vibrators 262 via cable 254. In FIG. 20, a particular embodiment of hand set 290 includes power switch 292 for providing power to the vibrators 262, activation switches 294a and 294b for independently activating neck vibrators 232 and low back vibrators 262, respectively, and paired indicators 296a and 296b, for example lighted marker bars, respectively in communication with switches 248 on the left and right side of low back assembly 204 (or alternatively, configured for tandem operation of paired vibrators). Hand set 290 enables the user to activate the neck and/or low back vibrators without first having to compress switches 248, thus allowing the inventive apparatus to be used as a relaxation and stretching device as well as an exercise device. Furthermore, when the inventive device is used for strengthening the user's lower back, indicators 296a-b visually alert the user when the user's lower back muscles exert sufficient compressive force to compress switches 248.

In more particular embodiments, the switch/force adjustment system incorporated in low back assembly 204 include one or more measurement elements that quantify the magnitude of the compressive force exerted by the users lower back on the switch/force adjustment system. In such embodiments, paired indicators 296a-b can include a display element that visually indicates the magnitude of the compressive force. Such embodiments assist the user in adjusting the compressive force exerted by each side of the user's lower back, in order to exert equal compressive force on each and thus optimize the strengthening exercises performed using the apparatus. Alternatively, as mentioned previously, the system can be configured for tandem operation in which the two sides of the users back are not independently monitored.

In particular embodiments, head/neck 206 and low back assembly 204 are used jointly, both being attached to mat 202. In the alternative, head/neck assembly 206 and low back assembly 204 can be used separately, either attached to mat 202 or by itself. More particularly, low back assembly 204 can be used as a separate device placed on a floor, an exercise apparatus, an automobile seat or other surface.

Figure 21:
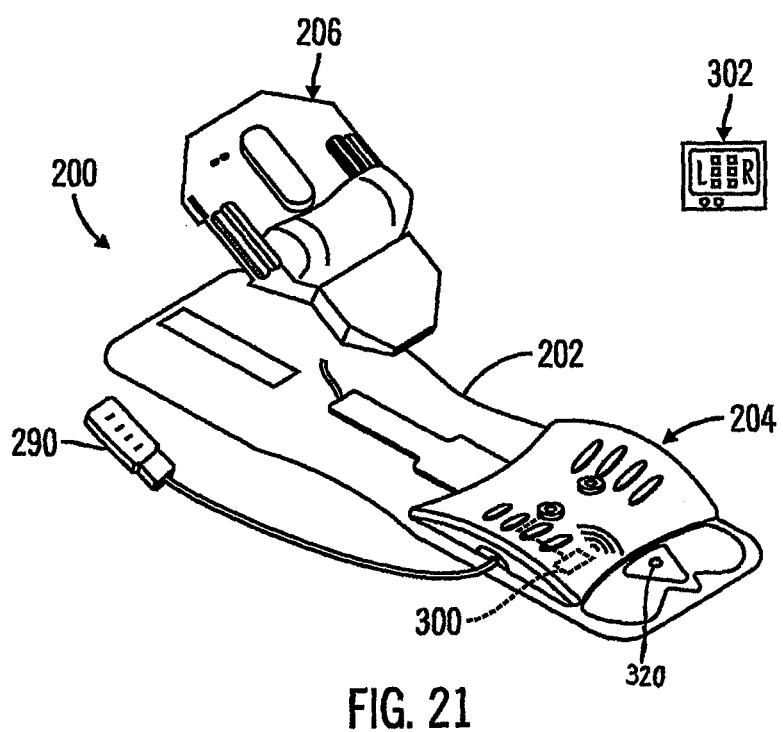
FIG. 21 is a schematic illustrating use of a television screen to provide a visual signal to a user.

The foregoing embodiments employ vibrator units as signal producing systems. Other signal producing systems, such as visual or auditory signaling units, can also be employed together with or in place of the vibrator units. For example, as shown in FIG. 21, a wireless transmitter 300 in communication with the switch/force adjustment system incorporated in low back assembly 204 transmits information defining the magnitude of the compressive force to a television screen 302 in a health club or other location. Television screen 302 then displays the information to the user.

Figure 22:
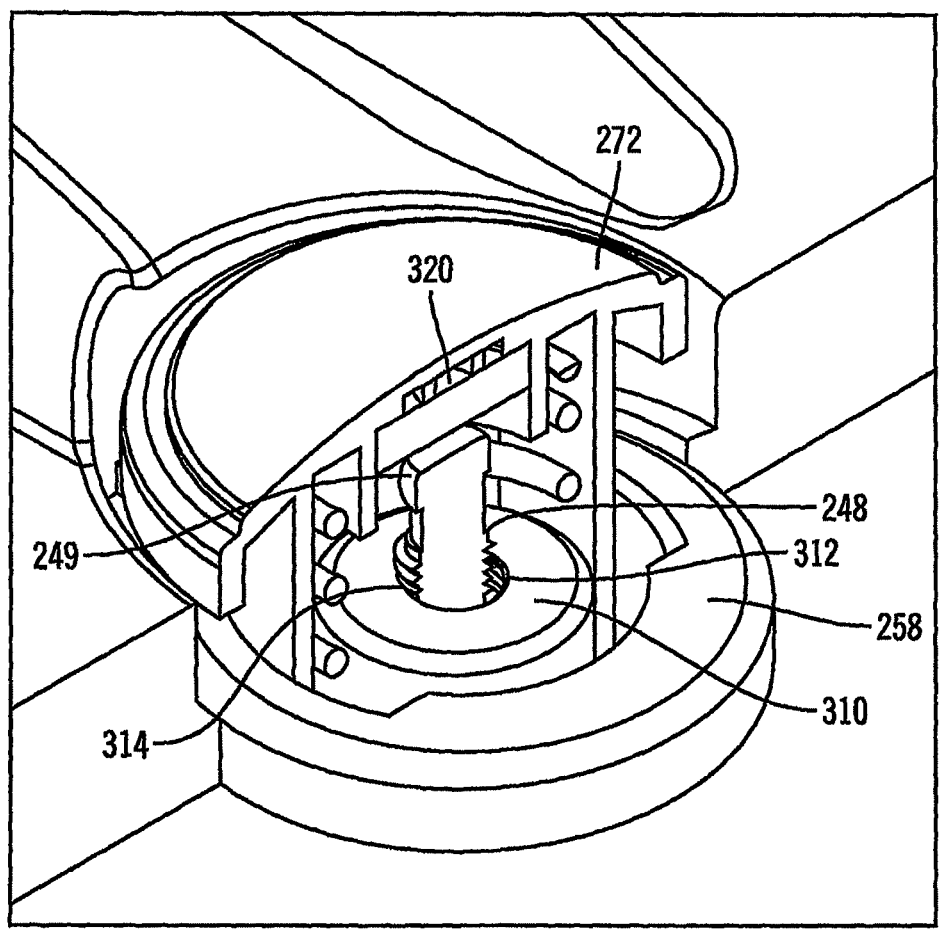
FIG. 22 is a perspective view illustrating an alternative embodiment of a switch/force adjustment system in which a switch is secured within a bushing.

FIG. 22 illustrates another alternative embodiment which provides additional support and protection for the switch 248. In this embodiment, a bushing 310 is mounted within and secured to switch mount 258. Bushing 310, in particular embodiments, comprises a metal, metal alloy, ceramic or other hard material, more specifically a material having a hardness greater than the hardness of the material forming switch mount 258. A threaded opening 312 is defined axially through bushing 310, and engages corresponding threads 314 formed on an outer surface of switch 248. According to more specific embodiments, a pair of bushings 310 support switch 248, with a first bushing being secured to switch mount 258 and a second bushing being secured to shell 246 and coaxially with the first bushing and with switch 248.

Embodiments making use of bushing(s) 310 afford additional support to switch 248, and also enable adjustment of the axial position of switch 248 as desired, particularly during manufacture of the assembly.

In further specific embodiments, a cushioning element 320 is provided between upper portion 249 of switch 248 and cap 272. Cushioning element 320 can comprise, for example, a foam material or another resilient material, and protects the switch 248 from excessive wear and other possible damage due to contact with cap 272.

In further particular embodiments, an additional activator 320 can be incorporated into the inventive device at a location corresponding to a user's lower sacrum. The additional activator 320, in very particular embodiments, activates one or more additional signal producing systems as described herein (e.g., vibratory, audio, visual, etc.). Such embodiments provide additional feedback to enable the user to maintain desired neutral spine positioning while exercising.

Additional embodiments enable information transfer to any desired display element, for example, a computer monitor, a laptop computer, a PDA, and the like. Such information can be transferred via a cable connection, a wireless transmitter, or any other desired mode of transmission. The information so transferred can also be further processed and stored.

Embodiments of the invention thus provide feedback for improving proprioceptive acuity and lumbo-sacral coordination.

A progressive exercise routine designed specifically for the inventive apparatus will allow the user to start with the short (e.g., 4 minute) drill series and progress at his own pace. Precision postural positioning for strong "neutral spine" occurs when the user re-educates the neuro-muscular system using the inventive apparatus.

The invention has been illustrated herein as a self-contained apparatus. However, the invention can also be incorporated into another object, including without limitation objects such as an exercise apparatus (e.g., an inclined rowing machine), an exercise bench, a chair, a bed, etc. The invention can also be separately produced and subsequently affixed to another object.

What is claimed is:

1. A postural awareness apparatus for strengthening the abdomen and spine of a user, the apparatus comprising
   a) a surface adapted to contact the user's back,
   b) a signal producing system that alerts the user when activated, and
   c) an activator coupled to the surface that activates the signal producing system for as long as compressive force applied to said activator from the user's back exceeds a predetermined level of compressive force, the predetermined level of compressive force indicative of muscle tightening by the user, the activator comprising
      (i) a switch having an upper portion,
      (ii) a compressible element having defined therein a compressible element opening, said compressible element at least partially surrounding said upper portion of said switch, and
      (iii) a cap for receiving the force exerted by the user's back, the cap adapted to secure said compressible element in a position at least partially surrounding said upper portion of said switch,
      (iv) wherein the switch is configured to activate the signal producing system for as long as the compressive force applied to said activator exceeds the predetermined level of compressive force, wherein
   said switch and said compressible element have longitudinal axes, said longitudinal axes being substantially collinear;
   said cap comprises an upper element and a plurality of arms, said arms each having a distal end comprising a locking element, and wherein each of said arms of said cap extends through a base opening defined in said base;
   said compressible element is disposed between said base and said upper element of said cap; and
   wherein said locking elements of said cap prevent unintentional disengagement of said cap from said base while permitting motion of said cap relative to said base substantially in the direction of said longitudinal axes of said switch and said compressible element thereby permitting said upper element of said cap to activate said switch when a compressive force in excess of said predetermined level is applied to said upper element.

2. The postural awareness apparatus of claim 1, wherein the surface comprises a low back assembly.

3. The postural awareness apparatus of claim 2 wherein said low back assembly comprises
   (i) a base having defined therein a base opening within which said switch is disposed, and (ii) a cushion having defined therein a cushion opening aligned with said base opening.

4. The postural awareness apparatus of claim 3, wherein said base comprises a raised portion in which said base opening is defined, and wherein said switch extends at least partially through said base.

5. The postural awareness apparatus of claim 4, wherein the cap further comprises an upper element and a plurality of arms, said arms each having a distal end comprising a locking element.

6. The postural awareness apparatus of claim 5 wherein said switch and said compressible element have longitudinal axes, said longitudinal axes being substantially collinear.

7. The postural awareness apparatus of claim 1, wherein said compressible element is selected from the group consisting of a spring and a disk comprised of a compressible substance.

8. The postural awareness of claim 1 comprising a plurality of activators, wherein said surface has a longitudinal axis and wherein a portion of said plurality of activators are located at opposed locations on either side of said longitudinal axis.

9. The postural awareness apparatus of claim 8 wherein said signal producing system comprises a plurality of vibrator units, a portion of said plurality of vibrator units being coupled to said surface at opposed locations on either side of said longitudinal axis.

10. A postural awareness apparatus according to claim 1, adapted to contact a portion of the lower back of a human user, the apparatus further comprising
    d) a base having defined therein a base opening, and
    e) a cushion having defined therein a cushion opening aligned with said base opening.

11. The postural awareness apparatus of claim 1, further comprising:
    at least one vibrator unit; and
    a control unit, the control unit comprising i) the activator, wherein the activator selectively activates the at least one vibrator unit, and ii) a display element that provides a visual indication when the at least one vibrator unit is activated, said display element optionally providing a visual indication of a magnitude of the compressive force applied to the activator.

12. The postural awareness apparatus of claim 8, further comprising an activator located substantially on the longitudinal axis at a position corresponding to a user's lower sacrum.

13. The postural awareness apparatus of claim 1, wherein the activator is responsive to a compressive force having a value within a selected range.

14. The postural awareness apparatus of claim 1 further comprising a control unit, the control unit comprising i) the activator, wherein the activator selectively activates at least one vibrator unit, and ii) a display element that provides a visual indication when the at least one vibrator unit is activated, said display element optionally providing a visual indication of a magnitude of the compressive force applied to said activator.

15. The postural awareness apparatus of claim 1, further comprising a head activator for receiving a compressive force received from the user's head, the head activator coupled to the surface that activates the signal producing system for as long as the compressive force applied to said surface from the user's head exceeds a second predetermined level of compressive force, the second predetermined level of compressive force indicative of neutral spine position of the user.

* * * * *